US008090426B2

(12) United States Patent
Felder

(10) Patent No.: US 8,090,426 B2
(45) Date of Patent: Jan. 3, 2012

(54) MICROELECTRONIC BIOSENSOR PLUG

(76) Inventor: Robin A. Felder, Charlottesville, VA (US)

(*) Notice: Subject to any disclaimer, the term of this patent is extended or adjusted under 35 U.S.C. 154(b) by 1313 days.

(21) Appl. No.: 11/588,974

(22) Filed: Oct. 27, 2006

(65) Prior Publication Data

US 2008/0103376 A1    May 1, 2008

(51) Int. Cl.
    *A61B 5/05* (2006.01)
(52) U.S. Cl. ............ 600/347; 600/345; 600/365; 604/8; 604/264; 604/294
(58) Field of Classification Search .......... 600/345–347, 600/365; 604/8, 264, 294; 128/887
    See application file for complete search history.

(56) References Cited

U.S. PATENT DOCUMENTS

| | | | |
|---|---|---|---|
| 3,769,961 A | 11/1973 | Fatt et al. | |
| 3,958,560 A | 5/1976 | March | |
| 5,258,788 A | 11/1993 | Furuya | |
| 5,297,554 A | 3/1994 | Glynn et al. | |
| 5,352,411 A | 10/1994 | Khuri | |
| 5,725,493 A | 3/1998 | Avery et al. | |
| 6,120,460 A | 9/2000 | Abreu | |
| 6,149,684 A | 11/2000 | Herrick | |
| 6,152,875 A | 11/2000 | Hakamata | |
| 6,312,393 B1 | 11/2001 | Abreu | |
| 6,423,001 B1 | 7/2002 | Abreu | |
| 6,544,193 B2 | 4/2003 | Abreu | |
| 6,579,235 B1 | 6/2003 | Abita et al. | |
| 6,681,127 B2 | 1/2004 | March | |
| 6,973,338 B2 | 12/2005 | Isenberg et al. | |
| 6,975,892 B2 | 12/2005 | Burd et al. | |
| 6,980,842 B2 | 12/2005 | March et al. | |
| 6,981,958 B1 | 1/2006 | Gharib et al. | |
| 2003/0211625 A1 | 11/2003 | Cohan et al. | |
| 2004/0039297 A1* | 2/2004 | Abreu | 600/558 |
| 2004/0072358 A1 | 4/2004 | Ballerstadt et al. | |
| 2004/0254516 A1* | 12/2004 | Murray et al. | 604/8 |

(Continued)

FOREIGN PATENT DOCUMENTS

WO    01/56463 A1    8/2001

(Continued)

OTHER PUBLICATIONS

"Noninvasive Photonic-Crystal Material for Sensing Glucose in Tears", Clinical Chemistry, 50(12); 2236-2237, (2004).

(Continued)

*Primary Examiner* — Patricia Mallari
*Assistant Examiner* — Michael D'Angelo
(74) *Attorney, Agent, or Firm* — Lerner, David, Littenberg, Krumholz & Mentlik, LLP

(57) ABSTRACT

A plug capable of providing information relating to a physical or chemical property of a body fluid, or the presence or amount of a molecular component therein in a living organism is disclosed. Specifically, one embodiment plug is capable of being inserted into a portion of a human eyelid in order to provide information relating to tear fluid is disclosed. This embodiment plug includes a body having a passage which allows for the natural flow of tear fluid therethrough. In addition, a sensing mechanism is provided which is capable of measuring, for example, glucose levels in the body of a patient through the analysis of the tear fluid. Such plug may further be designed so as to double as a punctual plug useful in preventing dry eye. Methods of utilizing and implanting such plugs are also disclosed.

21 Claims, 8 Drawing Sheets

U.S. PATENT DOCUMENTS

2005/0154269 A1  7/2005  Cameron
2005/0186333 A1*  8/2005  Douglas ................. 427/97.1
2008/0038317 A1*  2/2008  Chang et al. ............. 424/428

FOREIGN PATENT DOCUMENTS

WO  2006/031658  3/2006

OTHER PUBLICATIONS

Baca et al, "Techinical Briefs", Clinical Chemistry, 53(7); 1370-1383, (2007).

Baca et al., "Tear Glucose Analysis for the Noninvasive Detection and Monitoring of Diabetes Mellitus", Clinical Science, (2007).

Beetham WP. (1935) Filamentary keratitis. Trans Am Ophthalmol Soc, 33:413-435.

Cai O, Zeng K, Ruan C, Desai TA, Grimes CA. (2004) A wireless,remote query glucose biosensor based on a pH-sensitive polymer. Anal Chem 76:4038-4043.

Choy, "Water-Soluble Antioxidants in Human Tears: Effect of the Collectio Method", Invetigative Ophthalmology & Visual Science, 42(13); 3130-3134, (2001).

Chung, "Microfabricated Glucose Sensor Based on Single-Walled Carbon Nanotube", Mechanical Engineering Dept., Northwestern University, pp. 618-620 (2004).

Daubert et al, "Tear Flow Analysis Through the Upper and Lower Systems", Ophtalmic Plastic and Reconstructive Surgery, 6(3); 193-196, (1990).

Doane MG. (1981) Blinking and the mechanics of the lacrimal drainage system. Ophthalmology 88:844-85 1.

Dohlman CH. (1978) Punctal occlusion in keratoconjunctivitis sicca. Ophthalmology 85:1277-81.

Fayet B, Bernard JA, Ammar J, Karpouzas, Taylor Y, Abenhaim A, Renard G, Pouliquen Y. (1990) Treatment of chronic dry eye with temporary punctal plugs. J Fr Ophthalmol 13(3):123-133.

Foulds WS. (1961) Iintra-canalicular gelatin implants in the treatment of kerato- conjunctivitis sicca. Br J Ophthalmol 45 :625-627.

Freeman JM. (1975) The punctum plug: evaluation of a new treatment for the dry eye. Tans Am Acad Ophthalmolol Otolaryngol 79:874-879.

Fullard et al, "Protein Levels in Nonstimlated and Stimulated Tears of Normal Human Subjects", Investigative Ophtalmolgoy & Visual Science 31(6); 1119-1126, (1990).

Gilbard JP. (1985) Tear film osmolarity and keratoconjunctivitis sicca. CLAO J, 11:243-250.

Gilbard JP. (1989) Effect of punctal occlusion by Freeman silicone plug insertion on tear osmolarity in dry eye disorders. CLAO J 15:216-2 18.

Iguchi et al., "A flexible and wearable biosensor for tear glucose measurement", Biomed Microdevices, 9; 603-609, (2007).

International Search Report, PCT/US2007/022616.

Jones LT. (1957) Epiphora II. Its relation to the anatomic structures and surgery of the medial canthal region. Am J Ophthalmol 43:203-212.

Maguire LL, Bartley GB. (1989) Complications with the new smaller size Freeman punctal plug. Arch Ophthalmol 107:961-962.

Maurice OM. (1973) The dynamics and drainage of tears. Int Ophthal Clin 31:103-116.

Mitka, "Poor Patient Adherence May Undermine Aim of Continous Glucose Monitoring", JAMA, 298(6); 614-615, (2007).

Turberville AW, Frederick WR, Wood TO. (1982) Punctal occlusion in tear deficiency syndromes. Ophthalmology 89:1170-2.

Wang et al., "Highly Selective Membrane-Free, Mediator-Free Glucose Biosensor", Analytical Chemistry, 66(21); 3600-3603, (1994).

Wang, "Review: Glucose Biosensors: 40 Years of Advances and Challenges", Department of Chemistry and Biochemistry, New Mexico State University, (2000).

Willis RM, Folberg R, Krachmer JH, Holland EJ. (1987) The treatment of aqueous deficient dry eye with removable punctum plugs. A clinical and impression-cytologic study. Ophthalmology 94(5): 514-518.

Yee RW. (1994) Quantitative ocular microbial flora of dry eye patients pre- and post punctal occlusion. Mvest Ophthalmol Vis Sci 35(4):1691.

Zhu et al., "Tear Dynamics Model", Current Eye Research, 32; 177-197 (2007).

Supplementary European Search Report, EP 07861510, dated May 3, 2011.

* cited by examiner

PRE-BLINK

DURING BLINK

POST-BLINK

MICROELECTRONIC BIOSENSOR PLUG

BACKGROUND OF THE INVENTION

The measuring and monitoring of substances in and the physical attributes of certain bodily fluids is an important and sometimes necessary procedure in the medical field. For instance, the monitoring of blood sugar (e.g. glucose), glycated proteins, and other diabetes markers, can be essential in the prevention of diabetes-related end-organ complications in diabetics. Self-monitoring of such blood sugar levels has become relatively common and has necessarily reduced diabetic patients' dependence on medical professionals. However, such self-monitoring requires invasive, painful and tedious tasks, such as the lancing of the skin to obtain a blood specimen with an apparatus that must be kept sterile, and constantly carried by the individual. Thus, even patients having extreme types of diabetes (e.g., Type 1 Diabetes) often fail to monitor their blood glucose levels on a regular basis.

Inconsistent or absent blood glucose management in diabetic patients is estimated to cause billions of dollars in excess health care costs each year. It has thus prompted the development of certain technologies that aid patients in better monitoring their bodies markers for diabetic disease. For example, various devices and techniques have been developed, which are of a less invasive nature, for obtaining and/or measuring a specimen. Even these minimally invasive methods and devices have drawbacks. It has been reported by the American Diabetes Foundation that frequent testing with trend analysis is the single most valuable tool for maintaining good control and avoiding long-term complications of diabetes. However, many of these devices do not automatically record and track glucose levels on a regular time basis (e.g., minute by minute). Rather, these devices require some type of action on the part of the patient, and thus do not guarantee regular monitoring. Intermittent measurement of blood glucose fails to identify important peaks, valleys and trends that a continuous monitor could track in order to help predict impending hypoglycemic events, and facilitate improved metabolic control. As such, proposed devices and techniques may be ill-suited for optimal monitoring of glucose levels in diabetic patients.

U.S. Pat. No. 6,120,460 ("the '460 patent") teaches the utilization of a contact device placed on the front part of the eyelid in order to detect physical and chemical parameters of the body as well as the non-invasive delivery of compounds according to these physical and chemical parameters, with signals preferably being transmitted continuously as electromagnetic waves, radio waves, infrared and the like. The system utilizes eyelid motion and/or closure of the eye lid to activate a microminiature radio frequency sensitive transensor mounted in the contact device. The '460 patent teaches that the contact device remains in contact with the conjunctiva of the eye.

SUMMARY OF THE INVENTION

The present invention relates to a plug which is capable of being quickly and easily inserted through the punctum into the lacrimal canaliculus in either the inferior or superior eyelid of a patient. Unlike the prior art devices, the plug of the present invention does not involve direct eye conjunctiva contact (which is extremely sensitive) thus making it more comfortable, safer, and easier for a patient to tolerate. Once inserted, the plug remain functional for upwards of several months, and continuously provides information to a patient regarding a physical or chemical property of tear fluid, or the presence or amount of a molecular component therein. The device of the present invention exploits the fact that tear fluid closely mimics that of blood, and utilizes the tear fluid to provide information traditionally garnered from the analysis of blood. A patient may easily view results of information provided by the plug of the present invention, and act accordingly. For example, one embodiment of the present invention is adapted to provide a patient with continuous glucose measurements. Depending upon the levels of glucose present in the patient's system, an injection of insulin for instance may be administered.

A first aspect of the present invention is directed to a plug for monitoring tear fluid. The plug includes a body adapted for placement through the inferior or superior punctum in the eyelid, the body having an exterior surface and a passage formed therethrough. The plug also includes a sensor in fluid communication with the passage adapted to measure a physical or chemical property of tear fluid, or the presence or amount of a molecular component therein.

A second aspect of the present invention is directed to a method of monitoring a physical or chemical property of tear fluid, or the presence or amount of a molecular component therein. This entails providing a plug having a sensor adapted to measure the physical or chemical property of tear fluid, or the presence or amount of a molecular component therein, inserting the plug into or through a punctum of the eyelid, whereby tear fluid flows into contact with the sensor measuring the physical or chemical property of tear fluid, or the presence or amount of a molecular component therein, and transmitting information relating to the physical or chemical property of tear fluid, or the presence or amount of a molecular component therein to an external source.

A third aspect of the present invention is a biosensor system for implantation in a patient. The biosensor system includes a plug having a body adapted for placement within a portion of a human eyelid, the body having an exterior surface and a passage formed therethrough, and a sensor in fluid communication with the passage adapted to measure a physical or chemical property of tear fluid, or the presence or amount of a molecular component therein, and a receiver having a display. The plug transmits information relating to the physical or chemical property of tear fluid, or the presence or amount of a molecular component therein to the receiver for viewing by the patient on the display.

BRIEF DESCRIPTION OF THE DRAWINGS

A more complete appreciation of the subject matter of the present invention and the various advantages thereof can be realized by reference to the following detailed description in which reference is made to the accompanying drawings in which.

DETAILED DESCRIPTION

The present invention is intended for use in conjunction with a living organism. Although described herein in the context of an eye, such as an eye of a mammal (e.g., a human or livestock such as a cow) it is to be understood that the present invention may have uses in other bodily organs of various living organisms. For example, the present invention may be inserted in the salivary ducts to measure salivary substances or consistency, or mammary glands, seminal vesicles, or cowper's glands to measure secretions.

Figure 1:
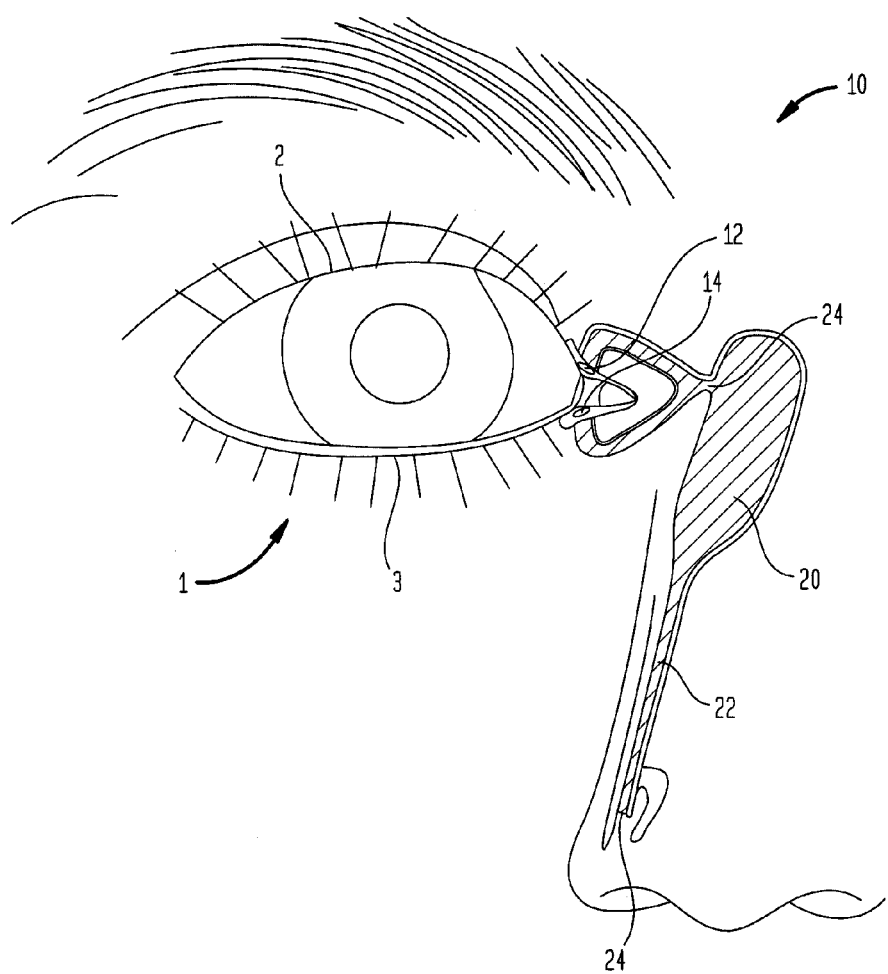
FIG. 1 is an illustration of certain anatomical portions of the human eye.

FIG. 1 depicts a human eye or eye ball 1 and certain anatomical portions associated with same. Specifically, FIG. 1 depicts human eye 1 having an upper lid 2 and a lower lid 3, as well as a lacrimal (tear) drainage system 10. In normal circumstances, the bulk of tear fluid in eye 1 is excreted by the lacrimal or tear gland (not shown), and tears are generally swabbed over the eye with every blink of lids 2 and 3. From the surfaces of eye 1, tears normally flow along the edge of lids 2 and 3 toward the nose (shown as element 4 in FIG. 1). Just before reaching the corner of eye 1, the tears are aspirated by the blinking process into lacrimal drainage system 10, which is essentially a miniature drainage network that prevents tears from continuously spilling over or rolling down an outer portion (the cheeks) of the face.

Figure 2:
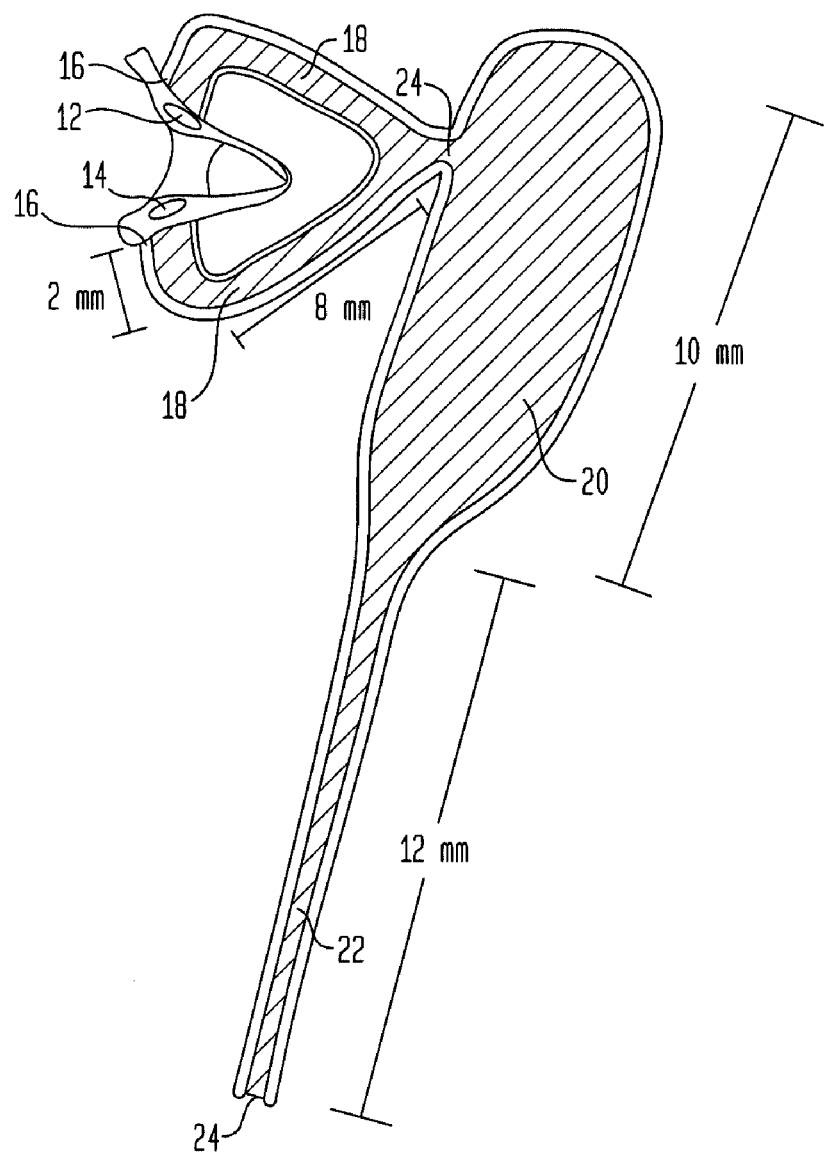
FIG. 2 is an enlarged illustration of the view of FIG. 1, with attention on the lacrimal drainage system of the human eye.

As is shown in FIG. 1, and in greater detail in FIG. 2, lacrimal drainage system 10 typically includes a superior punctum 12, an inferior punctum 14, two vertical canaliculi (superior and inferior) 16, two horizontal canaliculi (superior and inferior) 18, a lacrimal sac 20 and a nasolacrimal duct 22, all connected as shown in FIGS. 1 and 2. It is to be understood that these elements are being described as the most basic elements of system 10, and are only representative of some of the many components system 10 does in fact include. The operation of blinking of lids 2 and 3 generally aids in the draining of tears from eye 1 by creating a vacuum which aspirates the tear fluid through the punctum into the lacrimal canaliculi.

Figure 3A:
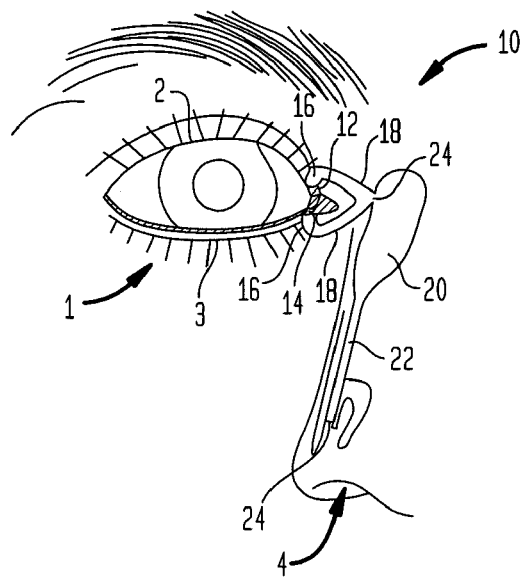
FIGS. 3A-3C are illustrations depicting the operation of the lacrimal drainage system in a human eye during blinking.
Figure 3B:
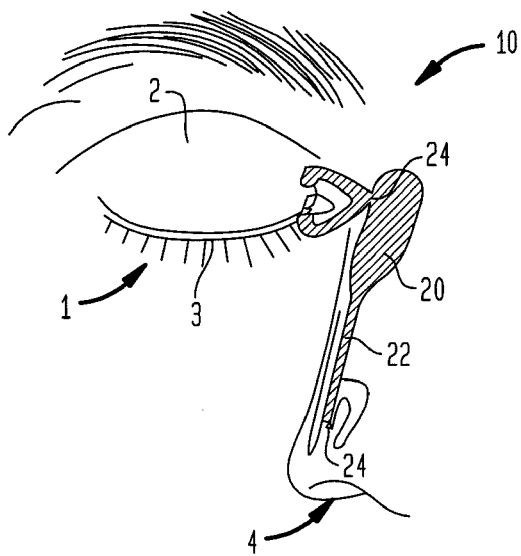
Figure 3C:
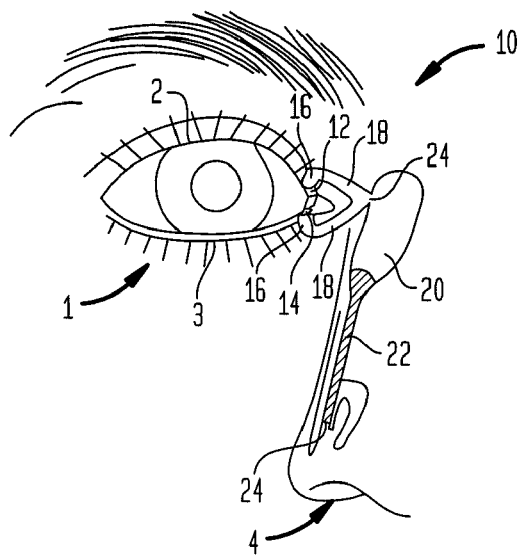

FIGS. 3A-3C depict eye 1 and lacrimal drainage system 10 during the different stages of a blinking operation. Specifically, FIG. 3A depicts a pre-blink state in which tears (shown as shaded areas) have already entered into the superior and inferior vertical canaliculi 16 through superior punctum 12 and inferior punctum 14, respectively. In a normal human eye, capillarity ensures that approximately 70% of the tear volume enters the inferior canaliculus, while approximately 30% of the tear volume enters the superior canaliculus. This is basically due to gravitational effects which tend to push tears into the inferior canaliculus when a person is vertical, and into both the superior and inferior canaliculus when a person is lying in a substantially horizontal position.

Upon blinking of lids 2 and 3, the attachment of the pre-septal orbicularis muscle (not shown) helps create positive and negative pressure in lacrimal sac 20, thereby sucking tears into it. This is shown in the view of FIG. 3B, and is often referred to as the tear pump. The force of gravity then helps keep sac 20 empty during post-blink, as is shown in FIG. 3C. In addition, during this post-blink state, the opening of lids 2 and 3 tends to create a negative pressure, thereby forcing tears to move from sac 20, through nasolacrimal duct 22, and ultimately into the nasal cavity (not shown). The volume of tear fluid depicted in the diagrams is not to scale and is shown for illustrative purposes only. True volumes depend on the subjects age, sex, physical state, and tear production rates. As is mentioned above, eye 1, nose 4 and system 10 all include additional components which may or may not aid in the application and drainage of tears to and from eye 1. For example, system 10 preferably includes several valves generally referred to in FIGS. 1 and 2 by reference numeral 24. These valves operate such that once tears pass therethrough, such fluid cannot return to eye 1.

While tears are no doubt important in keeping eye 1 properly lubricated, it has also been established that tears or tear solution located in an eye of a patient can be analyzed in order to garner information relating to other functions of the human body. The main component of the tear fluid is the aqueous layer which is an ultrafiltrate of blood containing electrolytes such as sodium, potassium, chloride, bicarbonate, calcium, and magnesium as well as amino acids, proteins, enzymes, DNA, lipids, cholesterol, glycoproteins, immunoglobulins, vitamins, minerals and hormones. Moreover, the aqueous layer also holds critical metabolites such as glucose, urea, catecholamines, and lactate, as well as gases such as oxygen and carbon dioxide. Furthermore, any exogenous substances found in the blood stream such as drugs, radioactive compounds and the like are also present in the tear fluid. Thus, in some cases, tears provide a less invasive alternative to blood or plasma as a source of bodily fluid. For example, the present invention may be utilized to take measurements of electrolytes, pH, osmolarity, body temperature, acid and lactate, creatine, lipids, blood gas, mediator of inflammation, endocrine hormones, liver and other tissue enzymes, inflammatory mediators, coagulation factors, albumin, lactoferrin, and proteins, among others. So, for instance, analysis of tears can determine the level of glucose in diabetics. The present invention will now be described in particular relation to this determination of glucose levels.

Figure 4:
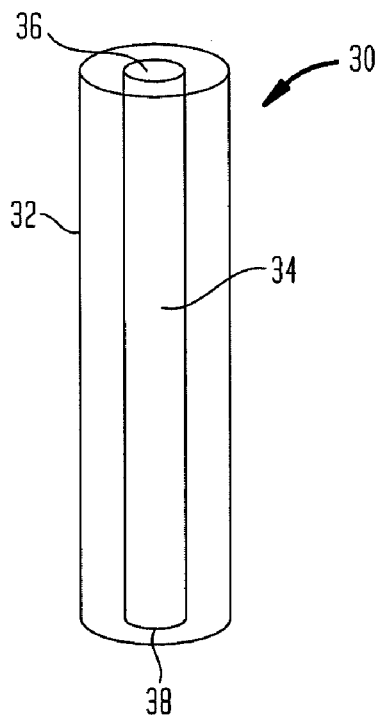
FIG. 4 is a perspective view of a plug in accordance with one embodiment of the present invention, with certain portions shown as transparent for illustrative purposes.

Referring to the remaining drawings, wherein like reference numerals refer to like elements, there is shown in FIG. 4 an exemplary biosensor plug according to the present invention, designated generally as reference numeral 30. Plug 30 is preferably designed for insertion into either the superior punctum 12 or the inferior punctum 14, in order to measure the glucose level in a patient by analysis of tears passing from eye 1 and through lacrimal drainage system 10. As is shown in FIG. 4, plug 30 includes an elongate cylindrical body 32 having a channel or passage 34 therethrough, beginning at an entry aperture 36 and continuing through an exit aperture 38. The illustration of plug 30 shown in FIG. 4 is a very basic depiction of a plug in accordance with the present invention.

Elongate cylindrical body 32 is preferably constructed of an inert, biocompatible material. Suitable material for the construction of body 32 include polymers, homopolymers, cross-linked polymers and copolymers of silicones, acrylic esters, polyurethanes and hydrocarbon polymers, among other materials. Body 32 is sized and shaped for insertion into either the superior punctum 12 or the inferior punctum 14, where it ultimately remains within one of the aforementioned canaliculi (e.g., two vertical canaliculi 16 and/or two horizontal canaliculi 18). Preferably, plug 30 and body 32 are designed for insertion into one of the vertical canaliculi 16. As shown in the FIG. 4, body 32 is elongate, with a relatively small diameter in order to promote comfortable insertion through one of the puncta and into one of the canaliculi. Dimensions for body 32 generally range between approximately 0.2 mm and 1.0 mm in diameter, and between approximately 1.5 mm and 2.0 mm in length. Of course, different patients may require smaller and/or larger plugs 30. Body 32 may also include microfabricated plastic or metal fibers which are designed as hair like protrusions, which may increase the adherence of plug 30 to the interior surface of any of the canaliculi or other bodily structure in order to prevent movement once the plug is put in place. As will be discussed more fully below in the section detailing problems associated with dry eyes, plug 30 may employ a body 32 which is configured and/or shaped to provide for other functions than that of simply the monitoring of glucose in tears.

Passage 34 is shown in FIG. 4 as extending in a straight fashion between entry aperture 36 and aperture 38 through the center of body 32. In other embodiments, passage 34 may be off-centered, curved, spiraled, tapered from entry aperture 36 to exit aperture 38 or from exit aperture 38 to entry aperture 36, wider in its center or other portion along its length, wider at its ends, and any combination of these configurations. Similarly, although passage 34 is depicted as being circular in its cross-sectional shape, it may be shaped in any suitable fashion. For example, passage 34 may have a square, rectangular, triangular or the like cross sectional shape. Preferably, passage 34 is designed to take advantage of or accommodate the natural flow of tears from eye 1 through lacrimal drainage system 10. Thus, passage 34 is preferably sized and shaped so as to allow normal flow of tears therethrough without the need for an additional force generator, such as a pump. In certain embodiments, passage 34 is circular and has a diameter of between approximately 0.2 mm and 0.8 mm. In other embodiments, plug 30 includes two or more passages, like passage 34, but which may be similarly or differently sized and/or shaped.

Figure 5:
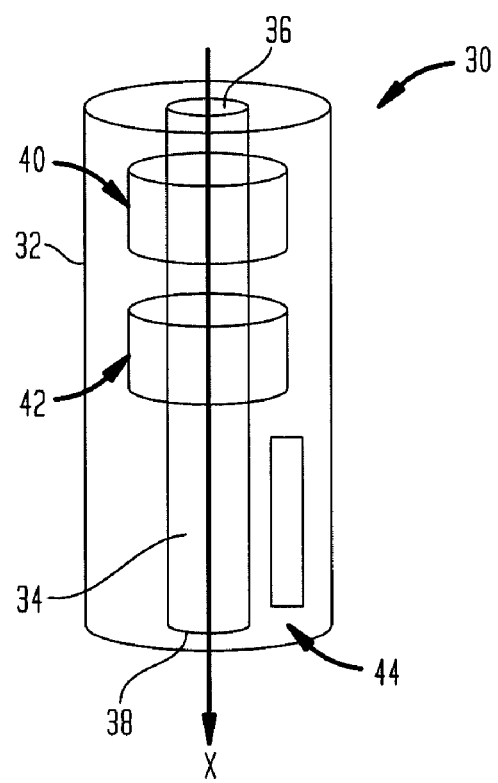
FIG. 5 is another perspective view of the plug of FIG. 4, with certain portions shown as transparent for illustrative purposes.

In addition to the basic structure discussed above, plug 30 includes several further internal components illustratively depicted in FIG. 5. While the above-described structure of plug 30 aids in taking advantage of the natural flow of tears, the following internal components aid in the measuring of a physical or chemical property of the tear fluid, or the presence or amount of a molecular component therein. For instance, plug 30 includes one or more internal components which act as sensors capable of sensing or otherwise determining the level of glucose present in tear fluid flowing through the plug. There are many different sensors employing sensing components that may be utilized. The sensor(s) is sized and shaped so as to fit within plug 30, analyze volumes of tear fluid generally in the range of 20 nl or less (which is generally regarded as the normal flow of tear fluid), and detect glucose therein (e.g., in concentrations within the range of 0.3 mg/dL to 15 mg/dL). Preferably, sensor(s) are very responsive (e.g., in less than 2 seconds), operates on a very small current (e.g., less than 1 microampere), and continuously measures glucose for a significant period of time (e.g., on the order of 3,000 hours) without fouling or losing sensitivity. Suitable sensor(s) are also designed so as to work in conjunction with other elements of plug 30.

The biocatalytic oxidation of glucose in the presence of glucose oxidase is a two step process consisting of enzymatic oxidation of glucose by glucose oxidase in which the co-factor flavin-adenine dinucleotide (FAD) is reduced to FADH.sub.2 followed by oxidation of the enzyme co-factor by molecular oxygen with formation of hydrogen peroxide. The reaction may be described as follows:

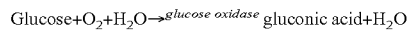

Glucose+$O_2$+$H_2O \rightarrow^{glucose\ oxidase}$ gluconic acid+$H_2O$

With catalase enzyme, the overall reaction may be described as follows:

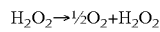

$H_2O_2 \rightarrow \frac{1}{2}O_2 + H_2O_2$

The signals can be transmitted using various transmission systems with an externally placed receiver demodulating the audio frequency signal to a voltage and the glucose concentration being calculated from the voltage and subsequently displayed on a LED display. An interface card can be used to connect the receiver with a computer for further signal processing and analysis. During oxidation of glucose by glucose oxidase, an electrochemically oxidable molecule or any other oxidable species generated such as hydrogen peroxide can be detected amperometrically as a current by the electrodes.

A variety of materials can be used for the electrodes such as silver/silver chloride coded cathodes. Anodes may be constructed as a platinum wire coated with glucose oxidase or they may be covered by an immobilized glucose oxidase membrane.

Glucose concentration can be measured either by electrochemical detection of an increase of an anodic current due to oxidation of the reaction product, hydrogen peroxide, or by detection of the decrease in a cathodic current due to the chemical reduction of the co-reactant, oxygen. Thus, the plug may contain an enzyme electrode that comes into contact with the tear fluid, and which measures the oxidation current of hydrogen peroxide created by the stoichiometric conversion of glucose and oxygen in a layer of glucose oxidase disposed inside the plug. A glucose sensor may be electrochemical in nature and based on a hydrogen peroxide electrode which is converted by immobilized glucose oxidase which generates a direct current depending on the glucose concentration of the tear fluid. The glucose enzyme electrode is responsive to changes in the concentration of both substrates of glucose oxidase, namely glucose and oxygen. Current generated by the enzyme electrode is proportional to the glucose concentration, and may be converted to a frequency audio signal and transmitted to a remote receiver.

The present invention may also entail use of an organic mediator such as ferrocene, which transfers electrons from glucose oxidase to a base electrode with subsequent generation of current.

One particular set of sensing components acting as a sensor will now be discussed. As is depicted in FIG. 5, plug 30 further includes an enzyme cartridge 40, an electrode 42, and electronics 44. For illustrative purposes, flow of tears in FIG. 5 is illustrated by arrow X. Enzyme cartridge 40 includes an enzyme or other chemical that reacts with glucose present within the flow of tears. While glucose oxidase is believed to be the best enzyme for converting glucose to measurable substances, other glycolytic enzymes and or catalysts may be used such as catalyse. In the preferred embodiment shown in FIG. 5, cartridge 40 is composed of a porous structure of glucose oxidase which reacts with glucose in the tear stream to form hydrogen peroxide. This porous structure may facilitate the reaction and in turn, allow the sensor to more accurately analyze the amount of glucose present in the tear fluid. As shown in FIG. 5, cartridge 40 is a hollow cylindrical shape with surfaces that align with passage 34. Hence, tear fluid entering through aperture 36 is naturally pumped through cartridge 40 and into contact with its particular enzyme (i.e., glucose oxidase). Other structures may be utilized, such as a solid cartridge having several passageways formed therethrough or being of a sufficiently porous structure to allow flow of tear fluid therethrough, and a structure which is offset within passage 34.

Figure 6:
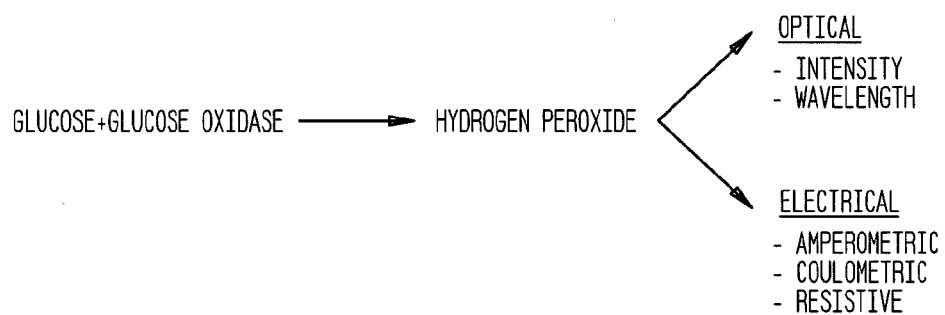
FIG. 6 is a diagram depicting an exemplary operation of an optical and electrical sensor utilizing but not limited to glucose oxidase.

Any bi-product (e.g., the aforementioned hydrogen peroxide composition) of the reaction between the tear fluid and cartridge 40 then impinges upon electrode 42, which is capable of analyzing the amount of bi-product and reporting such amount through an electrical connection (not shown) with electronics 44. Essentially, electrode 42, which may be composed of polished conductive metal or other conductive surface situated in a similar fashion as that of cartridge 40, further reduces or oxidizes the products of the initial glucose oxidation or reduction. In the above-mentioned preferred embodiment, the hydrogen peroxide bi-product interacts with electrode 42 so as to facilitate a change in, for example, the intensity or color (wavelength) of an emitted light, or to facilitate a change in an electrical current flow through the plug. The former is referred to as an optical sensor, and the latter as an amperometric or coulometric sensor. A graphical depiction of these two sensor types is shown in FIG. 6. Preferably, cartridge 40 is arranged linearly with respect to electrode 42 so as to prevent the products of the aforementioned glucose oxidation or reduction to foul the electrode. The result of either sensing technique is then transmitted (via a connection) to electronics 44, and ultimately, as will be discussed more fully below, to a readable receiver. This analysis of the tear fluid passing through plug 30 inherently provides for an analysis of the glucose content in the body or blood stream of a patient due to the correlation of blood and tear glucose concentrations, albeit that these are not temporally aligned. However, it is clear that other substances in the tear fluid may also be analyzed depending upon the type of cartridge 40 and electrode 42 being employed.

It is to be understood that different sensing components may also be utilized in conjunction with the present invention. For example, it is known to utilize carbon nanotubes to measure glucose levels. These sensors exploit the intrinsic optical and electrical properties of single-walled and multi-walled carbon nanotubes. Like that discussed above, such sensors utilize a chemical reaction that involves glucose oxidase (and the production of hydrogen peroxide). One specific sensor utilizing such technology employs carbon nanotubes that are coated in a monolayer of glucose oxidase to which ferricyanide is added. The ferricyanide is sensitive to hydrogen peroxide, the byproduct of the chemical reaction between glucose and glucose oxidase. The presence of hydrogen peroxide preferably changes the inherent optical properties or electron conductive properties of the carbon nanotube. Consequently, the intensity of a fluorescence or amount or electromotive potential of the electrons emitted by the carbon nanotube is a function of the glucose level. Other suitable glucose sensors employing different sensing components may also be utilized by plug 30, as long as such may be tailored to the particular use and specifications of plug 30.

Figure 7:
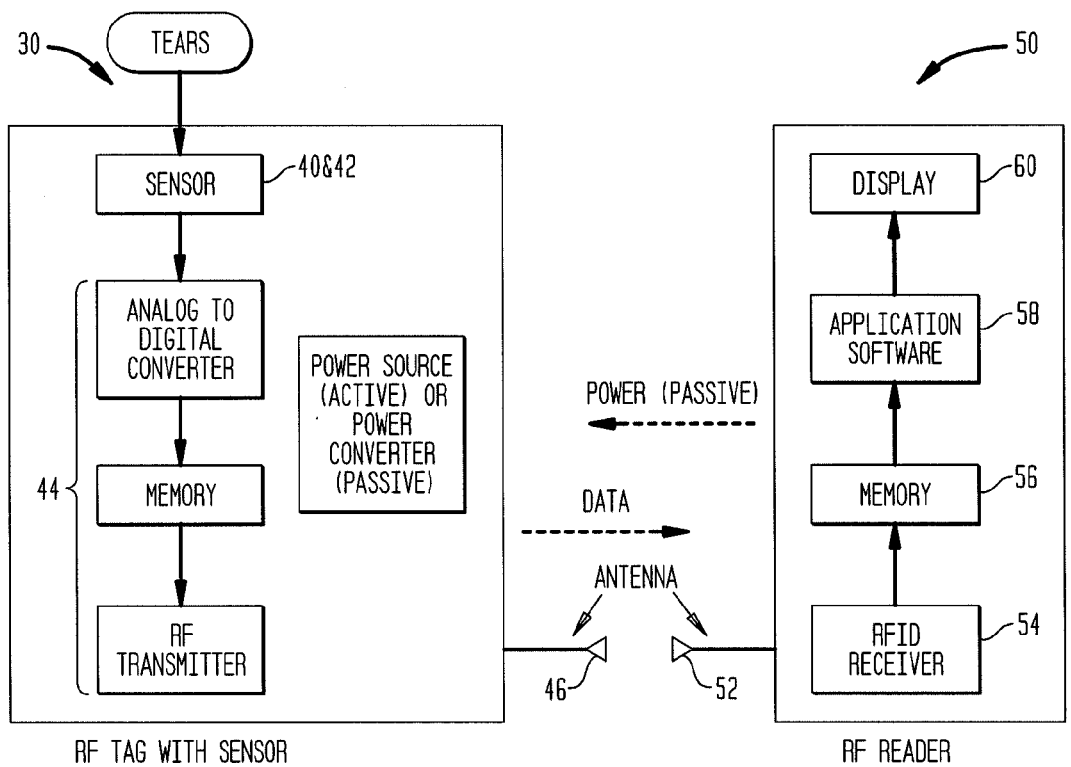
FIG. 7 is a block diagram depicting the relationship of various components of a plug and receiver in accordance with the present invention.

As is shown in the block diagram of FIG. 7, the aforementioned electronics 44 are preferably designed so as to transduce the information emanating from electrode 42 and to transmit such information to an external source (e.g., a receiver). For example, electronics 44 are preferably designed so as to convert an analog signal (if initially in this format) to a digital signal that is more appropriate for transmitting. In addition, electronics 44 preferably encompass a transmitter capable of transmitting such a signal. In preferred embodiments, electronics 44 is a radio frequency integrated circuit (RFIC) capable of wireless transmission of information. Broadly, however, many different types of transmitters can be used. RFIC's will be discussed more fully below. In short, electronics 44 facilitates wireless communication of data acquired by the glucose sensing technology (e.g., cartridge 40 and electrode 42).

RFIC's are one means for facilitating wireless communication, but the present invention is certainly not limited to the use of same. Like some of the other components of plug 30, the integration of RFIC in electronics 44 is dependent upon the certain of the properties of the plug. For example, these properties include the overall size of plug 30 (e.g., 2.0 mm×1.0 mm×0.5 mm), its power requirements (active vs. passive power), the carrier frequency to be utilized (e.g., 402-405 MHz (MICS band)), and the normal communications distance (e.g., 1.0-2.0 m) coupled with the associated antenna (discussed below). Generally, RFIC technology lends itself to relatively small devices. In fact, there is some thought by those of ordinary skill in the art that RFIC's will continue to become smaller and smaller. RFIC's may also be adapted for power by both active and passive power sources, where active devices typically require a battery for power and passive devices induce power from a received RF signal or light. While either type of power setup may be employed by plug 30, the latter is especially important given the size constraints of the plug itself. However, it is to be understood that a plug utilizing an RFIC powered by a battery may transmit signals over a further distance.

A carrier frequency is the frequency at which the RFIC typically communicates with an outside device, such as the reader discussed further below. While there are commonly used frequencies within the Industrial, Scientific and Medical (ISM) band of the electromagnetic spectrum, the FCC has allocated a specific band of frequencies for implanted medical devices. The Medical Implant Communications Service (MICS) band is typically from 402 to 405 MHz, and this band preferably supports high-speed data communications from devices implanted within the human body over distances on the order of several meters. Plug 30 clearly falls within this category of devices. Thus, many different RFIC's may be suitable for use in plug 30 for wirelessly transmitting output from cartridge 40 and electrode 42 to an outside receiver. One particularly suitable RFIC is sold under the product designation AMIS-52100 by AMI Semiconductor of Pocatello, Id.

Other wireless technologies may be utilized by plug 30 to transmit the information garnered by the operation of cartridge 40 and electrode 42. Of course, such technology must meet the same criteria that the above-discussed RFIC technology must. One example of such other technology is known as a wireless mote. These devices typically include complex circuitry, sophisticated networking capabilities and integration of various sensors. Often, wireless motes require a battery to power the complex circuitry, to facilitate wireless communication between nodes in a network and to power the sensors. Those of ordinary skill in the art would recognize that wireless motes can be utilized in place of an RFIC, and the particular wireless mote to be utilized could be selected based upon the constraints of plug 30.

Although RFIC's or other wireless communications devices may have built in antennas or the like, it is contemplated to provide plug 30 with an external antenna in order to improve transmission distance and/or clarity. In fact, proper antenna design, whether integrated with the wireless communicator or not, is important to the performance of plug 30. An antenna for use in accordance with the present invention is illustratively shown in the block diagram of FIG. 7 and labeled with reference numeral 46. Suitable external antennas for use with plug 30 may be a straight piece of wire cut at its center (a half-wave dipole), a wound piece of wire (a helix or coil antenna) or the like. Such external antennas may be attached to the end of plug 30 which is first inserted into a portion of eye 1 or attached at other portions of the plug. The former configuration for an antenna may be snaked down deep into one of the canaliculus without interfering with tear drainage or flow. An alternative embodiment may include an antenna that is initially rolled up or otherwise compressed into a small area during insertion. Once inserted, the antenna may be designed to unfurl or elongate down into the lacrimal duct in order to achieve a longer length of the antenna, for example, but not limited to the dissolution of a binder that holds the antenna to the punctal plug, or through the use of memory wire that changes shape depending on temperature.

Likewise, plug 30 may be powered by a number of different energy sources. For example, and active source, such as a battery, may be utilized. Alternatively, power cells which convert either light or body heat into energy could be suitable active power sources. Of course, the use of an active power source such as these examples must fit within plug 30, and therefore must rather small. In this regard, a passive power source could be employed, with power being delivered to plug 30 through an RFIC or the like. Such passive sources need not be included in plug 30, but typically, transmission distance with same is largely minimized as compared to plugs employing batteries. The use of a passive power source could require a patient to place an external device at or near plug 30, or within a suitable range. The latter could allow for operation of plug 30 without the requirement on the part of the patient to make a positive act. As light and heat converting power sources become more efficient, it is anticipated that a passive power source will be incorporated into the device.

Ultimately, plug 30 preferably transmits information garnered from tear fluid passing therethrough to a receiver system. As is shown in FIG. 7, receiver system (designated by reference numeral 50) preferably includes an antenna 52, a receiver 54, a memory 56, a software package 58 and a display 60. Of course, other embodiments of receiver system 50 may utilize additional, fewer and/or different components. Preferably, antenna 52 and receiver 54 are capable of receiving a signal transmitted from plug 30. As plug 30 has been discussed in relation to the measurement of glucose levels in tears, the signal transmitted from plug 30 relates to same. However, it is clear from the above discussion that a plug in accordance with the present invention may be designed and used to measure different materials and/or conditions within many different living organisms. FIG. 7 depicts both electronics 44 and receiver 54 as being RF technology, but as is discussed more fully above such could be a different technology suitable for transmission of the necessary information.

Memory 56 is capable of storing information received from plug 30. This is important in revisiting or tracking certain of the information relating to the glucose levels in a person over time. Software package 58 processes information received from plug 30 so that such can be displayed on display 60. It is to be understood that depending upon the graphics being displayed on display 60, software package 58 may vary. Similarly, package 58 may vary with the type of information and/or signal being received from plug 30. In the embodiment shown in FIG. 7, plug 30 is powered by passive power provided by receiver system 50. Thus, system 30 is placed within a certain distance of plug 30 in order to generate a signal to be received. In this regard, plug 30 includes a power converter for converting the passive power received from system 50. The distance required for operation of plug 30 can vary and in certain embodiments is several feet, in which case system 50 is kept on or near the patient in order to receive continuous readings.

Receiver system 50 may be a stand-alone device directed solely to receiving information from plug 30, or such may be built into another device. For example, system 50 may be a component of a larger device, such as a cell phone, personal data assistant, watch, television, MP3 player, computer or the like. Those of ordinary skill in the art would readily recognize how system 50 could be built into one of the aforementioned other technologies. Thus, a patient could be provided with a device not only useful for measuring the level of glucose, but also for performing other tasks or providing other benefits. As is mentioned above, plug 30 and system 50 are capable of taking regular interval readings of the glucose level of a patient's body, and thereafter storing and displaying such information to a patient. It is contemplated that patients could be provided with charts, graphs, tables or the like relating to the various glucose measurements taken. Such would clearly be dependent upon software package 58 and display 60. Many data displaying means are well-known and widely utilized, and the present invention may employ any suitable one. It is noted that a memory, like memory 56 could also be included within plug 30 in order to store information relating to the glucose measurements. This information could thereafter be downloaded upon an interface between plug 30 and system 50. A system that operates in this fashion would only require intermittent communication between plug 30 and system 50.

In addition to measuring and displaying information relating to the glucose level in a patient, the present invention may serve other benefits. Tuning back to FIGS. 1-3, when a tear gland (not shown) and/or system 10 does not operate properly, dryness of eye 1 may become a problem. Dry eye is a debilitating condition which often causes patients to have symptoms such as a feeling of dryness, and/or a feeling of having a gritty or foreign body in the eye. Dryness of the eyes often results when there is a paucity of lubricating tear fluid produced in eye 1. Treatment of dry eye can be the continuous administration of lubricating fluid by the patient, or more conveniently by placing devices in the superior or inferior puncta of the affected eye. More particularly, devices such as punctal plugs have been developed to aid in increasing tear availability to the eye in patients with failing tear production, loss of tear production due to Lasic surgery, Sjögren's syndrome, drug induced dry eye, and filamentary keratitis. It is contemplated to provide a plug which employs a body that exhibits the properties of known punctal plugs. There exist several form factors for punctual plugs, which those of ordinary skill in the art would readily recognize could be incorporated into the plugs of the present invention.

Figure 8:
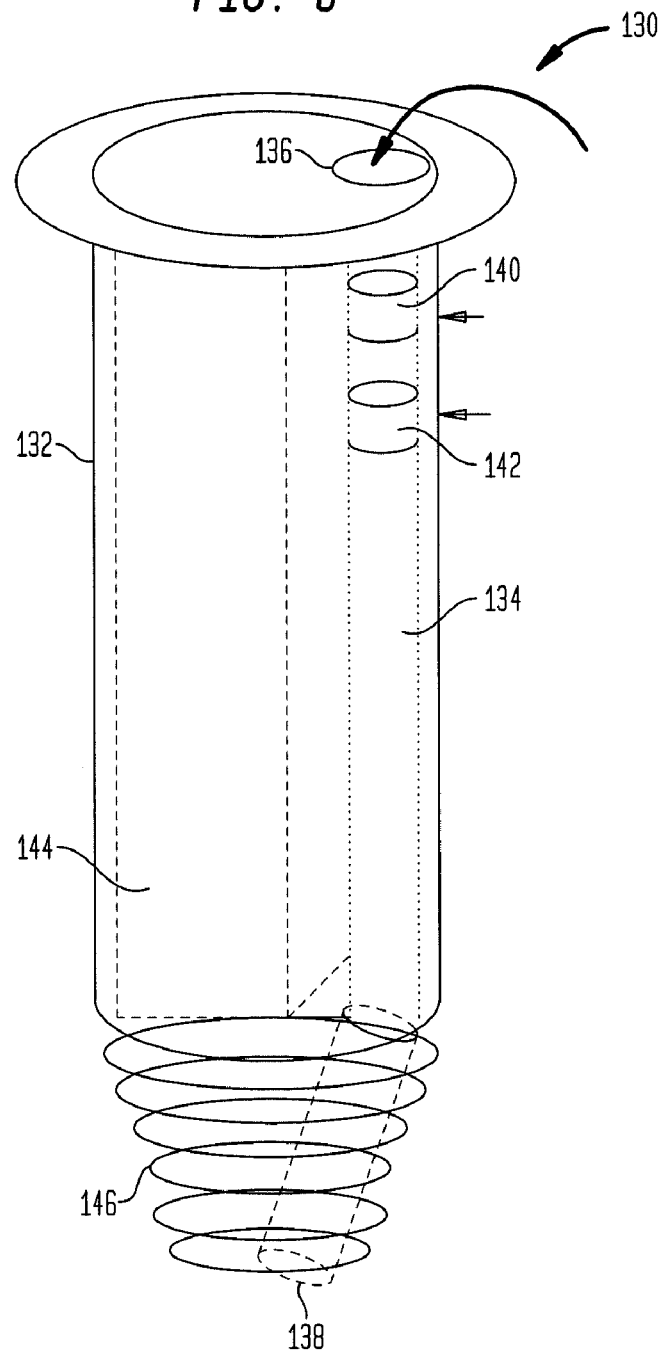
FIG. 8 is a perspective view of a plug according to another embodiment of the present invention, with certain portions shown as transparent for illustrative purposes.

For example, FIG. 8 depicts another embodiment in which plug 130 includes a body 132 shaped so as to act as a punctal plug when placed within one of the canaliculi of the eyelid. It is to be understood that in this embodiment plug 130 includes several components similar to those discussed in relation to plug 30. As such, like reference numerals have been used within the 100-series of numbers. For instance, plug 130 includes a body 132 having a passage 134 extending between apertures 136 and 138. Additionally, plug 130 further includes an enzyme cartridge 140, an electrode 142, electronics 144, and an antenna 146, and the operation of each component and plug 130 as a whole remains substantially similar. However, plug 130 also acts like a punctal plug suitable for alleviating problems associated with dry eye conditions. Specifically, the shape of body 132 of plug 130 acts so as to allow for somewhat of a build up of tear fluid in the exterior aspect of the eye 1 before draining through system 10. Therefore, plug 130 serves two purposes in subjects with dry eye, namely it will be useful in monitoring tear chemistry, as well as providing improved eye lubrication from increased availability of tears in the exterior aspects of the eye.

Plug 130 could also be equipped with a means to adjust the flow of tears through the device. For example, plug 130 could utilize two members disposed within passage 134, one capable of rotating in relation to the other to cause the passage to increase or decrease its diameter. This is similar to a camera iris, and could therefore increase or decrease the flow of tears therethrough to effectively determine the amount of tears that remains in the exterior aspects of the eye 1. The flow passage may be active or passive. A passive system would require the physician or manufacturer, or other professional involved in the patients medical care, to set the diameter of the flow orifice based on the relative dryness of the patient's eye. Alternatively, the system may be active in that the system would actively adjust the size or flow through the orifice based on the relative dryness of the patient's eye. Dryness may be ascertained in a number of ways including tear sodium (or other component) concentration and/or tear flow.

Figure 9:
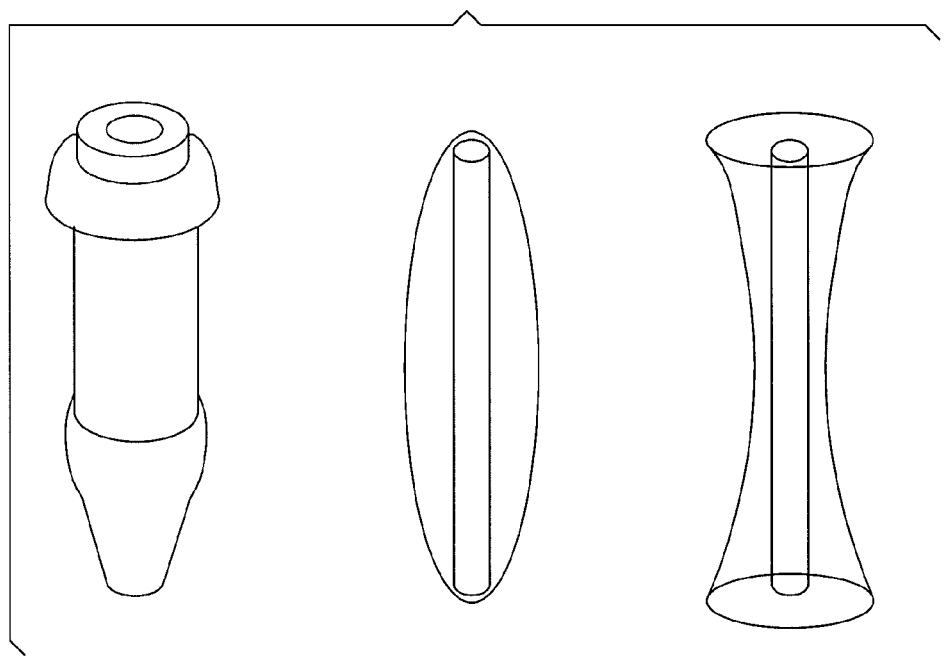
FIG. 9 is an illustration depicting other plug designs in accordance with other embodiments of the present invention.

FIG. 9 depicts three additional body shapes which may be employed in connection with a plug according to the present invention. These examples are merely shown for illustrative purposes, and all other configurations suitable for aiding in the prevention of dry eye may clearly be utilized. In addition, a plug according to the present invention may include certain exterior structure aids in keeping the device in place, once implanted.

Plugs in accordance with the present invention, such as plugs 30 and 130, are preferably easily inserted into a patient by any trained physician, but preferably by a trained ophthalmologist. A plug of the present invention may be provided in a kit with all tools necessary for insertion of same. Subsequent to examining the eye to determine the particular eye geography and to ensure the lack of any medical conditions likely to prevent proper use of the present invention, the physician selects a suitably sized plug. This may vary depending upon the patient, and can be determined through the use of a provided (in a kit) microscope having a gauge for determining the diameter of the particular punctum through which the plug will be inserted. In addition, separate tools may be provided for verifying the size of the puncta. It is noted that a patient having such a procedure done could be completely anesthetized or could simply have a local anesthetic applied to the eye in question.

Figure 10:
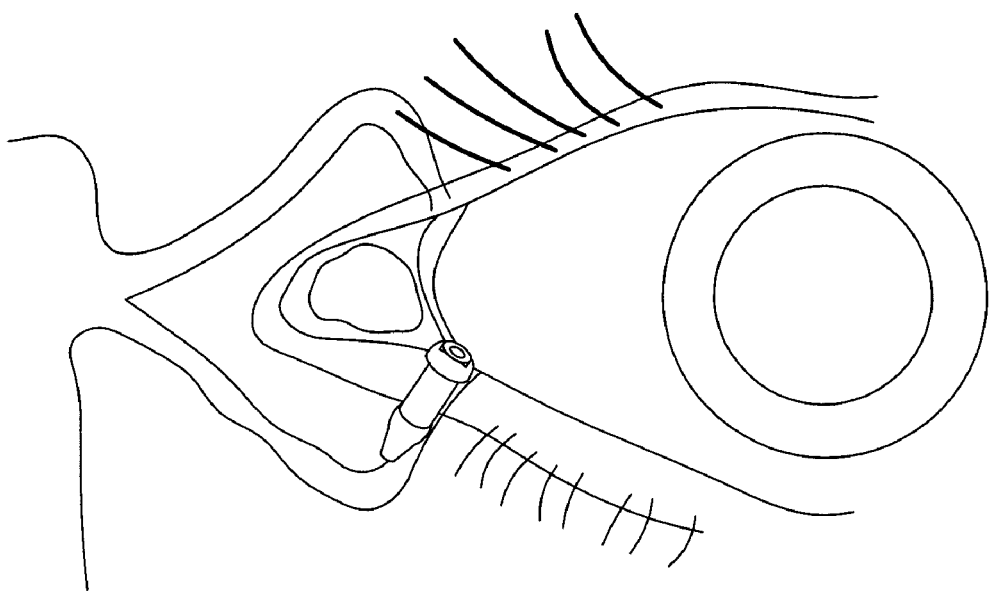
FIG. 10 is an illustration of the human eye with a plug in accordance with the present invention being disposed in a portion thereof.
Figure 11:
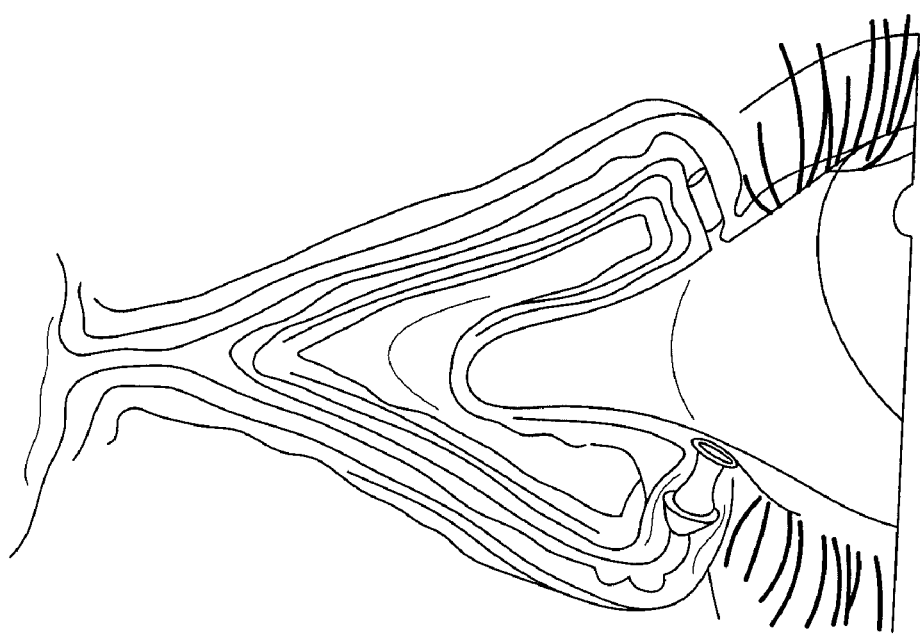
FIG. 11 is another illustration of the human eye with two plugs in accordance with the present invention being disposed in different portions thereof.

Once the correct size of the plug is determined, such is preferably inserted with the aid of an insertion tool. Such tools may include simple structures such as forceps or the like, or the tool (not shown) may have an elongate handle, a flange, and means for attaching to the plug. In the latter case, during insertion, the tool is slightly twisted to ensure smooth insertion. Once the flange of the insertion tool contacts an eyelid (2 or 3) of eye 1, the plug is completely in place. A release mechanism provided in the insertion tool may then be activated to release the plug therefrom, and conclude the insertion procedure. Thereafter, the plug and its sensing components may be calibrated and linked with a receiver (like receiver system 50). A fully inserted plug in accordance with the present invention is shown in FIG. 10. Likewise, FIG. 11 depicts two fully inserted plugs, in different portions of an eye 1. It is to be understood that more than one plug may ultimately be inserted in a single eyelid, as is shown in FIG. 11, or one plug could be placed through either punctum. Similarly, each eyelid of a patient may be provided with one or more plugs according to the present invention, thereby bringing the maximum total of plugs be used to four.

The present invention provides for a microelectric biosensor plug that is capable of measuring a presence or amount of a material or a condition with a living organism, in a minimally invasive, pain-free, comfortable, passive and continuous fashion. In certain embodiments, a plug according to the present invention may be inserted into a portion of a human eyelid in order to continuously and passively monitor a physical or chemical property of tear fluid, or the presence or amount of a molecular component therein. This is particularly important to diabetics, as glucose is one material that may be monitored in tear fluid. In addition, a plug in accordance with the present invention may be coupled with a receiver capable of receiving wireless transmissions from the plug. This provides a system of continuously monitoring and recording readings taken by the plug for glucose or other materials.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A plug for monitoring tear fluid comprising:
   a body adapted for placement through a punctum of a human eyelid, the body having an exterior surface, a passage formed therethrough, an entrance aperture and an exit aperture, the entrance and exit apertures in fluid communication with the passage; and
   a sensor in direct communication with the passage, the entrance aperture and the exit aperture, the sensor adapted to measure a physical or chemical property of tear fluid, or the presence or amount of a molecular component therein.

2. The plug of claim 1, wherein at least part of the sensor is exposed to the passage such that the sensor is in fluid communication with the passage.

3. The plug of claim 1, wherein the passage is centered within the body.

4. The plug of claim 3, wherein the passage is circular shaped.

5. The plug of claim 1, wherein the body is a punctal plug.

6. The plug of claim 5, wherein the punctal plug is adapted to actively or passively prevent dry eye.

7. The plug of claim 5, wherein the punctal plug is adapted for insertion through either the superior or inferior punctum.

8. The plug of claim 1, wherein the sensor is adapted to measure a glucose level in the tear fluid.

9. The plug of claim 8, wherein the sensor includes a cartridge having glucose oxidase.

10. The plug of claim 9, wherein the sensor further includes an electrode.

11. The plug of claim 10, wherein the electrode includes a plurality of carbon nanotubes.

12. The plug of claim 10, wherein the cartridge and the electrode are in fluid communication with the passage.

13. The plug of claim 12, wherein the cartridge is adapted to react with glucose in the tear fluid to create hydrogen peroxide.

14. The plug of claim 13, wherein the electrode is adapted to react with the hydrogen peroxide to vary an optical output or an electrical output.

15. The plug of claim 12, wherein the cartridge and the electrode are cylindrically shaped and confront the passage.

16. The plug of claim 12, wherein the cartridge is constructed of a porous material.

17. The plug of claim 1, further comprising an electronics module in communication with the sensor, the electronics module capable of transmitting information from the sensor to an external source.

18. The plug of claim 17, further comprising an antenna in communication with the electronics module.

19. The plug of claim 18, wherein the external source is a receiver having a receiver antenna and a display.

20. The plug of claim 19, wherein the electronics module is an RFIC.

21. A biosensor system for implantation in a patient comprising:
a plug having a body adapted for placement through a punctum of a human eyelid, the body having an exterior surface and a passage formed therethrough, an entrance aperture and an exit aperture, the entrance and exit apertures in fluid communication with the passage, and a sensor in direct communication with the passage, the entrance aperture, and the exit aperture, the sensor adapted to measure a physical or chemical property of tear fluid, or the presence or amount of a molecular component therein; and
a receiver having a display,
wherein the plug is capable of transmitting information relating to the at least one property of the tear fluid to the receiver for viewing by the patient on the display.

* * * * *